United States Patent [19]

Silverman

[11] Patent Number: 4,615,856
[45] Date of Patent: Oct. 7, 1986

[54] METHOD FOR FORMING AN INDIVIDUALLY CONTOURED CORRECTIVE SEAT FOR A WHEELCHAIR

[76] Inventor: Michael W. Silverman, 414½ Arlington St., Chicago, Ill. 60614

[21] Appl. No.: 760,245

[22] Filed: Jul. 29, 1985

Related U.S. Application Data

[62] Division of Ser. No. 524,861, Aug. 19, 1983.

[51] Int. Cl.$^4$ .................. B29C 33/40; B29C 39/10; B29C 67/22
[52] U.S. Cl. ............................ 264/222; 264/46.8; 264/511; 264/102; 264/267; 264/322
[58] Field of Search ............ 264/321, 222, 46.8, 264/102, 267, 322, 511

[56] References Cited

U.S. PATENT DOCUMENTS

3,830,896 8/1974 Flicker et al. .................. 264/54 X
4,347,213 8/1982 Rogers, Jr. .................... 264/222 X

Primary Examiner—Philip Anderson
Attorney, Agent, or Firm—Emrich & Dithmar

[57] ABSTRACT

An improved method for making custom molded seat cushions wherein a bead-filled latex bag is used as a trail buttocks supporting cushion and likewise another bead-filled latex bag is used as back-supporting cushion in a frame which is similar in function to the seat frame of the chair. An impression of a desired portion of a user's body is formed on each of the bags and air is removed from the bags thereafter to fix the impression. A positive mold of the individual's respective backside and buttocks impression are made. Corrective changes may be made either to the latex bag impression as it is being formed or the positive mold impression. The positive mold impression is then utilized along with a mold frame to mold a custom fitted seat cushion for the individual who will utilize the wheelchair. The cushions are then press fit into their respective seat frames and an individualized custom molded wheelchair seat is formed which provides for correctively positioning the individual in full surface contact between the body and seat to minimize or rid the possibility of bed sores, and to place the client in a functional position.

3 Claims, 23 Drawing Figures

METHOD FOR FORMING AN INDIVIDUALLY CONTOURED CORRECTIVE SEAT FOR A WHEELCHAIR

This is a division of application Ser. No. 524,861, filed Aug. 19, 1983.

BACKGROUND OF THE DISCLOSURE

This invention relates generally to improvements in wheelchairs, and more particularly, to improvements in correctively, custom molded wheelchair seats which are adapted for growth of individuals using the wheelchair, and for quick release mounting between the seat and wheelchair.

Heretofore, what may be described as beanbag type cushions have been utilized to form contoured impressions of the human body, as shown in U.S. Pat. No. 3,830,896. However, such contoured cushions have not included changes made in the impressions formed for providing corrective positioning to the individual for whom the molded cushion is formed. Likewise, the necessity for filling the beanbag after the individual has been positioned in the forming seat is negated by performing the shape of the backsupporting portion of the cushion while controlling the amount of negative air pressure therein.

Multimember, modular seating systems for the handicapped have been previously developed, as shown in U.S. Pat. No. 4,234,228. However, the cushions, disclosed therein are not custom molded to fit the individual utilizing the seat, and the articulation provided for the chair is one of angular articulation between individual pads, rather than an expansive changeability in the chair. Such known articulated seating systems for wheelchairs have been very expensive, and have not provided a means for expanding the size of the seat, or the spatial relation between the buttocks-supporting portion and backsupporting portion thereof, to accomodate the rather rapid growth of children. As a result, it has hertofore been necessary, in many instances, to purchase an entire new seat, at a substantial expense, when the user undergoes a growth spirt which is so common with children.

Therefore, a need has developed for an improved cushion seating arrangement for use in a wheelchair, and particularly one which provides for growth of the user without the necessity of making frequent major repurchases. It is therefore an object of the present invention, generally stated, to provide a new and improved custom molded seating apparatus for use in a wheelchair.

BRIEF SUMMARY OF THE INVENTION

The invention is directed to a removable seat for use on a wheelchair. The seat includes a seat frame having a substantially vertical backsupporting portion, and a substantially horizontal buttocks-supporting portion with cushion means mounted on the respective frame portion for providing a contoured body receiving surface. An invention resides in the improvement comprising means on the backsupporting portion for vertically adjustably positioning the back portion relative to the buttocks-supporting portion, and means on the buttocks-supporting portion for horizontally adjustably positioning that portion relative to the backsupporting portion.

The invention is further directed to a method for forming an individually contoured corrective seat for use by a disabled person. The seat is of the type having a frame including a substantially vertical backsupporting portion, and a substantially horizontal buttocks-supporting portion hingedly connected thereto with each portion adapted to retain at least one resilient cushion-like member. The method comprises the steps of: positioning a human being on a seat-forming frame having back and bottom deformable bags positioned thereon with each bag including a mass of bead-like material therein in order to form impressions on the bags of the back and buttocks respectively of a human being; making corrective changes to at least one of said bags to shape the contour of same to provide for corrective positioning of the human being in the final contoured-corrective seat; evacuating air from the back and bottom bags respectively to interlock said bead-like material into a form retaining condition; forming a positive mold of the back and buttocks by applying a setable mastic material to the impressions on the bags and allowing same to set; positioning the positive to the mold in spaced relation to the back and bottom portions of the seat forming frame to define a cavity therebetween; and filling the cavity with a setable fluid material while allowing same to cure into correctively-contoured back and bottom cushions.

BRIEF DESCRIPTION OF THE DRAWINGS

The features of the present invention, which are belived to be novel, are set forth with particularity in the appended claims. The invention may best be understood from the following detailed description of a currently preferred embodiment thereof, taken in conjunction with the accompanying drawings, wherein:

DETAILED DESCRIPTION OF THE PREFERRED EMBODIMENT

Referring to FIGS. 1-7, the improved, custom-formed wheelchair seat 25, constructed in accordance with the present invention, is shown mounted on a wheelchair 26 by means of a plurality of quick-connect trunnion mounts 27—27. Seat 25 includes a back-supporting frame 33, a buttocks-supporting frame 34, and a pair of L-shape hinge members 35, 36 which maintain the back and buttocks supporting frames in predetermined spatial relation to one another while providing for adjustable spatial and angular relation therebetween. The back-supporting frame 33 and buttocks-supporting frame 34 are made in predetermined stock sizes and may be identical or differ in size depending on the user's needs.

Figure 1:
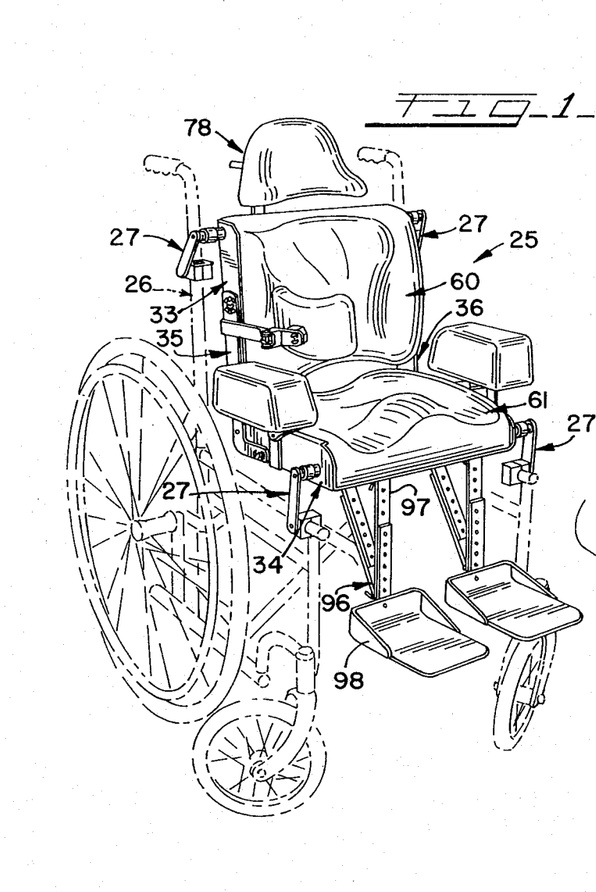
FIG. 1 is a perspective view of a contoured corrective seat assembly constructed in accordance with the present invention, as it appears mounted in a wheelchair.
Figure 2:
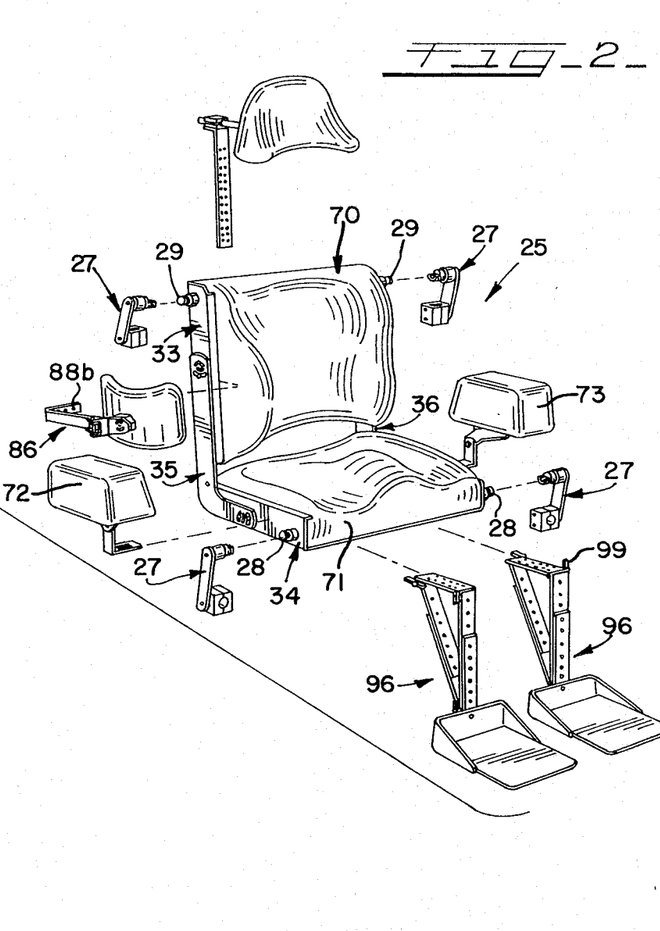
FIG. 2 is an exploded perspective view of the custom-contoured seat assembly shown in FIG. 1.
Figures 3, 4, 5:
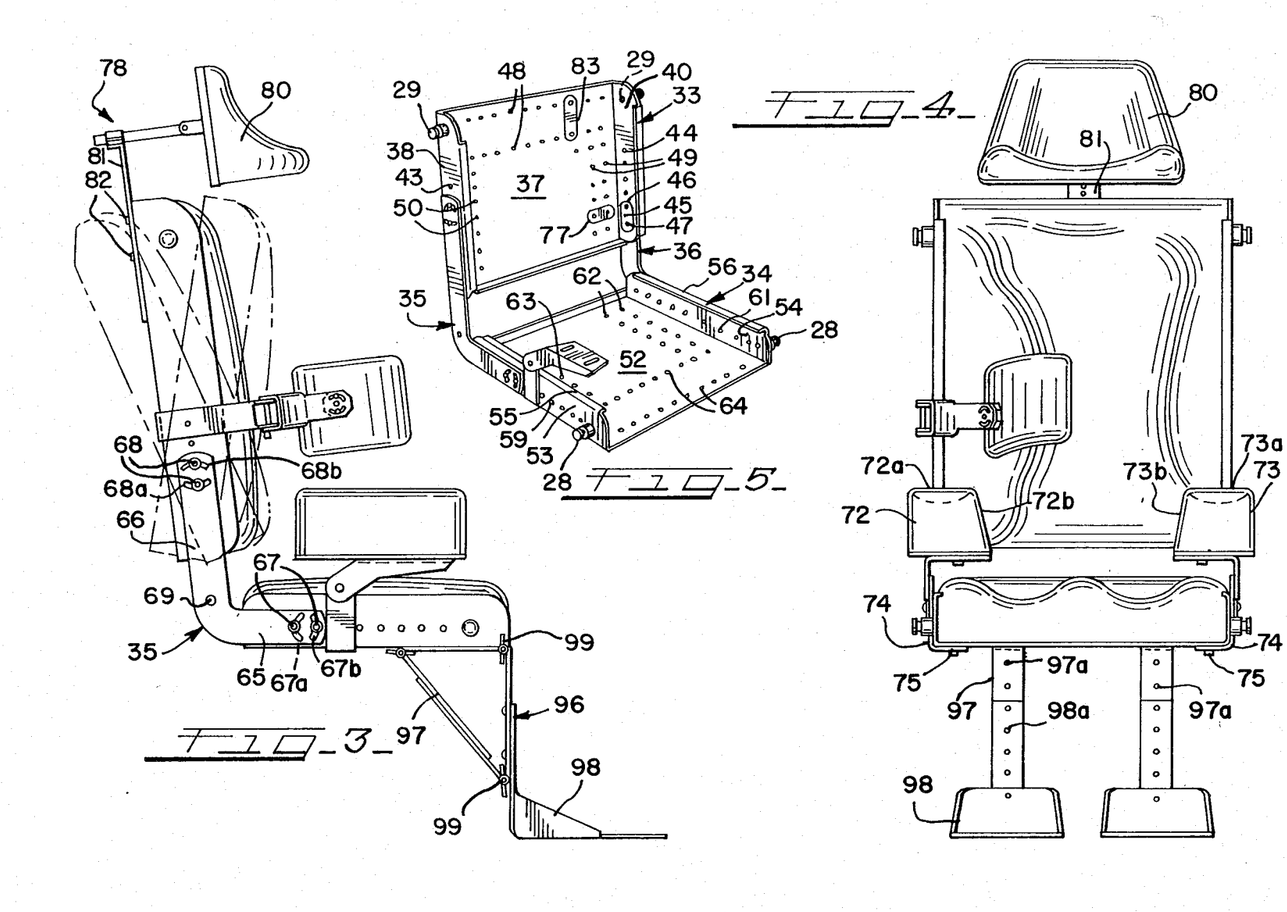
FIG. 3 is a side-elevational view of the seat assembly of the present invention shown in FIG. 1.
FIG. 4 is a front-elevational view of the seat assembly shown in FIG. 1.
FIG. 5 is a perspective view of the seat frame with the cushions removed therefrom.

Referring to FIG. 5, back-supporting frame 33 includes a generally planar rectangular back or web centersection 37 and opposed vertical flanges 38, 40, respectively, which extend forwardly at right angles from the opposed side boundaries of the central web 37. Each flange includes thereon toward the top thereof a substantially cylindrical trunnion 29, 29, extending laterally outwardly thereof for quick releasable connection to trunnion mountings 27—27, a plurality of aligned spatially related apertures 43—43, 44—44, respectively, provide for retaining the back-supporting frame to the respective hinges 35-36, respectively, by means of links 45—45 (only one shown) having like threaded apertures 46-47 therein for retaining threaded fasteners 68—68 therein. Additional aligned apertures 48—48, 49—49 and 50—50, forming a generally U-shape grid are adapted to retain other members, to be discussed in greater detail below, onto the frame. Lastly, the back-supporting frame flanges 38-40 each include a distal cushion-retaining rib 38a, 40a, respectively, extending 90 degrees inwardly from the forward edge of each flange. As a result of these features, the back-supporting frame 33 will maintain a back-supporting cushion positioned therein, be quickly releasably retained by trunnions 28-29 to a wheelchair frame, and be adjustably mounted in a desired spatial and angular relation to through hinges 35-36, a like shaped buttocks-supporting frame member 34.

As also shown most clearly in FIG. 5, the buttocks-supporting frame 34, depending upon the needs of the user, may be identical or substantially similar in shape to the back-supporting frame 33. Frame 34 includes a central-rectangular, horizontally-positioned web section 52 vertical flanges 53, 54, extending from the opposed side edges thereof, and a pairs of ribs 55-56, extending inwardly from the top distal edges of flanges 53-54, respectively, for retaining a seat cushion positioned centrally therein. Each vertical flange 53, 54 has a laterally extending trunnion 28, 28, respectively, positioned near the front end of the flange, and a plurality of apertures 59—59 and 61—61, which are adapted to retain the lower portions of hinges 35 and 36 in predetermined adjustable spatial and angular relation to the back-supporting frame 33, the mounting between hinges 35, 36, and buttocks supporting frame is accomplished by threaded fasteners and links 45, shown in connection with the back-supporting frame 33. The series of spaced double rows of apertures 62—62, 63—63, and 64—64, roughly in a U-shape are utilized to mount arm rests and foot rests to the frame, as will be shown in more detail below.

As shown most clearly in FIGS. 1-4, each L-shaped hinge 35, 36 (with hinge 35 shown for explanation) includes a horizontally-extending base 61 and a vertically-extending arm portion 62. Adjacent the distal end of the base 65 are a pair of arcuate slots 67a-67b, adjustably retained by threaded fasteners 67—67. Adjacent the distal end of the upwardly-extending arm member 66 are a second pair of arcuate slots 68a-68b, adjustably retained by threaded fasteners 68—68. An aperture 69 on L-shape hinge 35 may be used as s seat belt mounting, as shown in FIG. 3.

The dual pivotal mounting of back-supporting frame 33 and the buttocks-supporting frame 34 with relation to hinges 25, 26, provides heretofore unknown amounts of flexibility and adjustability to the shape of the complete seat. Also, as shown in broken line in FIG. 3, the plurality of spatially related apertures 43, 44, on back-supporting frame 33, and 59, 61 on buttocks-supporting frame 34, allow movement of the vertical frame up and down and the horizontal frame inwardly and outwardly to provide a proper size and shape seat for a user, and for growth of an individual utilizing the seat.

Referring to FIGS. 2, 4, 6, and 7, trunnion mounts 27, each include a conventional clamp 30 having dished or oval clamping surfaces which is adapted for selectably releasable fixed mounting to a conventional wheelchair or square-tubed stroller, linking member 31 rotatably mounted to clamp 30, and a quick-release connection composed of a threaded shaft 41, extending normally from link 31 and having a recess 41a on the distal end thereof into which the end of a trunnion 28-29 may be inserted and engaged, and an internally threaded collar 42 which, when extended over the recess 41a and into engagement with the base of trunnion 28, retains the trunnion in the recess. A knurled or otherwise roughened outer surface on collar 42, provides for hand maneuvering of same along the threads on shaft 41.

The remainder of the seat of applicant's invention includes a custom-formed, back-supporting cushion, generally indicated at 70 and a custom-formed, buttocks-supporting cushion, generally indicated at 71, which removably mount in frame members 33, 34, respectively, and a plurality of peripheral items, including left and right thigh support-arm rest members 72, 73, respectively, which selectably mount onto either the buttocks-supporting frame member 34 or the back-supporting frame member 33, by means of pairs of articulated arm members 74–75, including a base 74a–75a which is adjustable affixable to either seat frame by common threaded fasteners retained through slots in the base, and a pad holding member 74b–75b which is adjustably, swingably mounted to the base in a manner similar to the swingable mounting of chest supporting member 86 discussed below. Each arm rest pad and pad holding member may be selectably released to swing upwardly out of the way of a path for transferring an individual in or out of the seat, and then returned to a body supporting position. The upper inwardly dished surfaces 72a, 73a, respectively, of the thigh support-arm rest members 72, 73, may be utilized to locate and rest the chair user's arm and elbow thereon while the sloped but substantially vertical side 72b, 73b of each respective arm support is utilized to support the thighs of the user, allowing each ingress and exit when the pads are not swung upwardly out of the way. With the extreme base of adjustability of the seat assembly of the present invention, the only tool required for adjustment is a wrench, and adjustments may be made in the field at the user's situs.

Referring to FIGS. 7–13, other accessories mountable and demountable to the chair, in an adjustable manner similar to the arm rest members, include a neck-head brace assembly 78, including a contoured neck pad 80 thereon which is adapted to conform to the curvature of the user's neck and head-bottom. Pad 80 is moulded around a malleable frame (not shown) which is bendable to conform to the user's neck and head shape. Neck brace assembly 78 further includes an adjustable head-support mounting 81, which is retained on the back side of the back-supporting frame 33 by threaded fasteners 82—82 extending through mounting 81 and apertures 48—48 on frame 33 to be retained by link 83. An extension rod 82, which is adjustably pivotally mounted at 83 to the back of pad 80 and slidably and selectively, rotatably retained on the top of mounting 81 by clamp 84. The double row of apertures 48—48 and 81a–81a, with the spatial distance between apertures 81a being one-half the spatial distance between apertures 48 in both directions provide for abundant adjustability, both vertically and laterally. As shown most clearly in FIG. 13, by switching the alignment of apertures from the left vertical column to the right vertical column on mounting 81, the mounting may be adjusted laterally in increments one-half the width of the distance between apertures 48—48.

As shown in FIGS. 1–5 and 8–9, a chest or body supporting member, generally indicated at 86, which is adjustably mountable on the back of frame 33, includes a curved cushion 87, which like neck support pad 80, includes a malleable frame (not shown), and an articulated mounting linkage 88–90 between the frame 33 and cushion 87. The L-shaped base 88 of the articulated mounting linkage includes a distal foot 88a, including a plurality of elongate mounting slots 88b, in FIG. 2, therethrough similar to those shown in connection with articulated arm rest supports 74–75. Base 88 is adjustably mounted to back supporting frame 33 by threaded fasteners and link 77 through apertures 49—49, 50—50 in a manner similar to the mounting of the previously noted accessory items. Mid-link 90 is mounted at one end to L-shape arm 88 by means of pivot pin 91 for horizontal pivotal movement, and is mounted at its opposing end to cushion 87 for rotational movement therebetween around pin 93 with angular adjustment between the cushion and link being variable by means of a cam 92, which is coaxial with and sandwiched between the cushion 87 and mid-link 90. A spring loaded stop mechanism 91a, mounted on mid-link 90 adjacent one end of pin 91, selectably, releasably engages apertures in a flanged sleeve 89, concentrically mounted with pin 91, to allow pivotal movement between base 88 and mid-link 90 when desired.

Figures 6, 7, 8, 9:
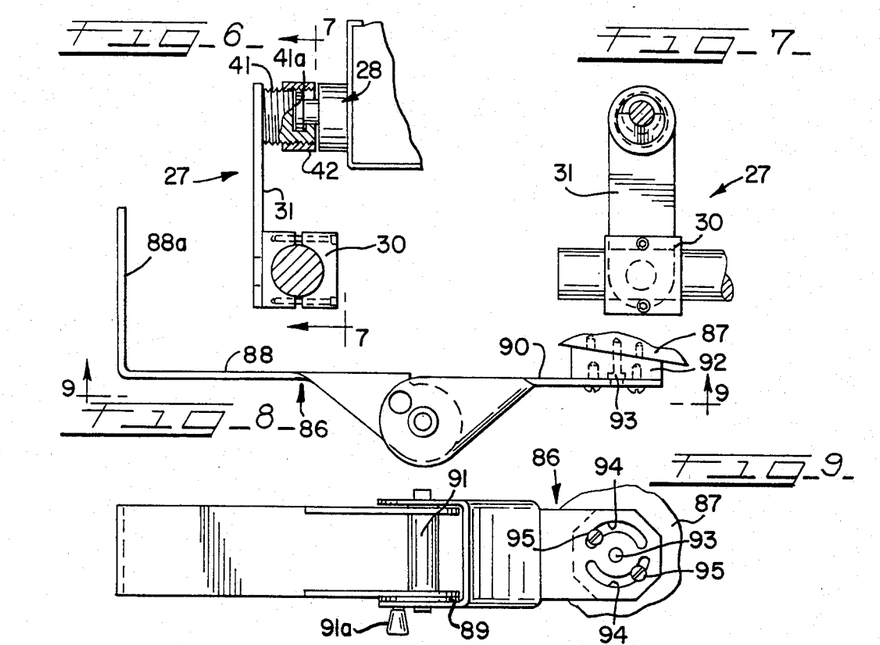
FIG. 6 is an enlarged fragmentary elevational view of the lower left quick-connection coupling shown in FIG. 1 with portions cut away to show the seat retaining mechanism.
FIG. 7 is a cross-sectional view taken substantially along lines 7—7 of FIG. 6.
FIG. 8 is an enlarged fragmentary plan view of the chest support bracket shown in FIG. 2.
FIG. 9 is a cross-sectional view taken substantially along lines 9—9 of FIG. 8.
Figures 10, 11, 12, 13:
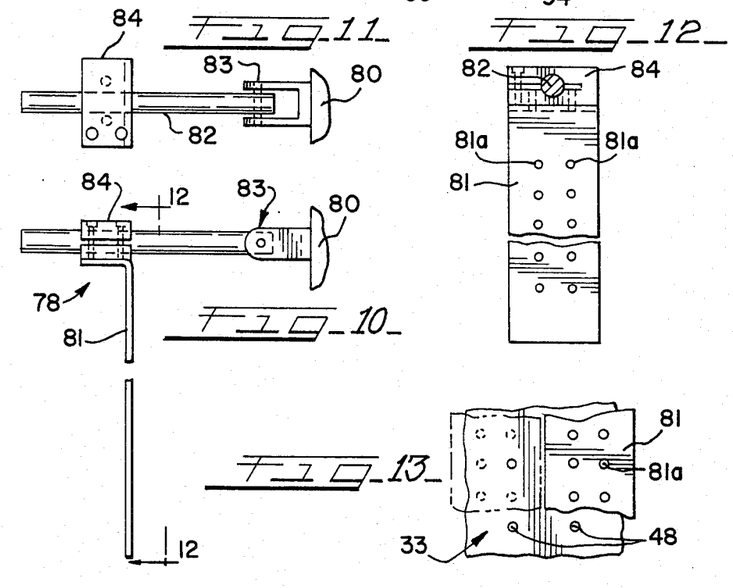
FIG. 10 is an enlarged fragmentary elevational view of the headrest mounting shown in FIG. 2.
FIG. 11 is an enlarged fragmentary plan view of the headrest mounting shown in FIG. 2.
FIG. 12 is a cross-sectional view taken substantially along line 12—12 of FIG. 10.
FIG. 13 is a fragmentary detail view of a portion of the seat frame of FIG. 5 showing frame-bracket alignment and adjustability therebetween.

The rotation of cam 92 relative to mid-link 90 approximates 180 degrees and is limited by a pair of arcuate slots 94—94 positioned through mid-link 90 surrounding an aperture for pin 93 in spatial relation thereto. Screws 95—95 mount into the back side of cam 92, ride in slots 94—94 and may be tightened into binding relation with the side edges of the slots when fixed positioning is desired. The opposed distal ends of slots 94—94 provide stops preventing further rotation between the cam 92 and mid-link 90. Pin 93 is threaded into cushion 87 at one of a plurality of threaded apertures to provide for rotational or fixed positioning therebetween and for length adjustment, as desired. Loosening screws 95—95 and/or cushion 87 from pin 93 allow the cushion 87 to be rotated until the fit of the cushion against the user is proper and comfortable. Then, the screws may be turned to fix the cushion 87 and cam 92 relative the mid-link 90.

Referring to FIGS. 1–5, a pair of adjustable foot rests 96—96 are mounted by the afore-disclosed threaded fasteners and links (not shown) fastened through apertures 64—64 adjacent the front of buttocks-supporting frame 34 so as to depend therefrom. Each foot rest 96 includes an adjustable triangulated base 97 which is hinged at its corners and has overlapping distal ends forming the hypotenuse thereof. A plurality of apertures 97a are positioned all along the base for providing adjustability to the foot rest. A stirrup 98 is mounted on the front of base 97 by conventional fasteners and, as a result of the multitude of apertures 98a on the stirrup and base, is adjustable in its vertical positioning. By lessening or increasing the overlap of the distal ends of base 97, stirrup 98 may be moved arcuately for user's comfort as desired. The corners of triangulated base 97 are held together by push pins 99 to provide ease of disassembly and adjustment.

Thus, the new and improved quickly mountable-demountable seat of the present invention has been shown and described as it mounts onto a wheelchair of conventional manufacture.

Figure 23:
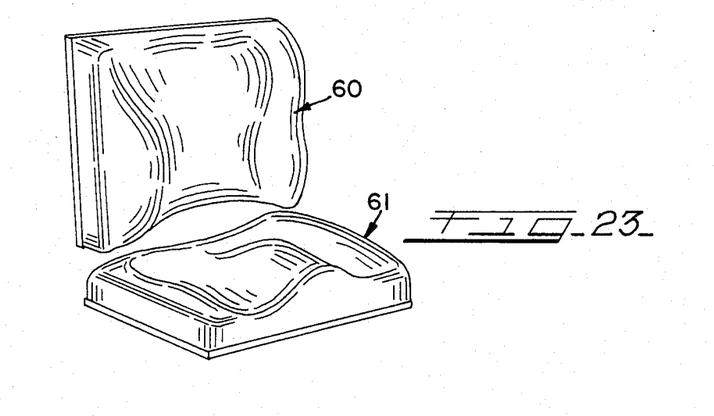
FIG. 23 is a perspective view of the finished, custom molded cushions of the present invention.

Referring to FIG. 23, and more generally to the method disclosed in FIGS. 14–23, the improved seat of the present invention includes a custom-formed, back-support cushion 60 having a generally rectangular outline sized for being press fit into the back-supporting frame 33. Each cushion has an outer frontal surface 127, preferably formed of a vinyl material, which is heated and stretched into the desired shape to provide a seamless cushion cover. The bulk of the cushion is made of polyurethane foam which is poured into the desired shape and expands and sets to produce the custom-moulded cushions 60 and 61 in the shapes desired, as will be disclosed more fully hereafter by explanation of the preferred method of moulding means.

Figures 14, 15:
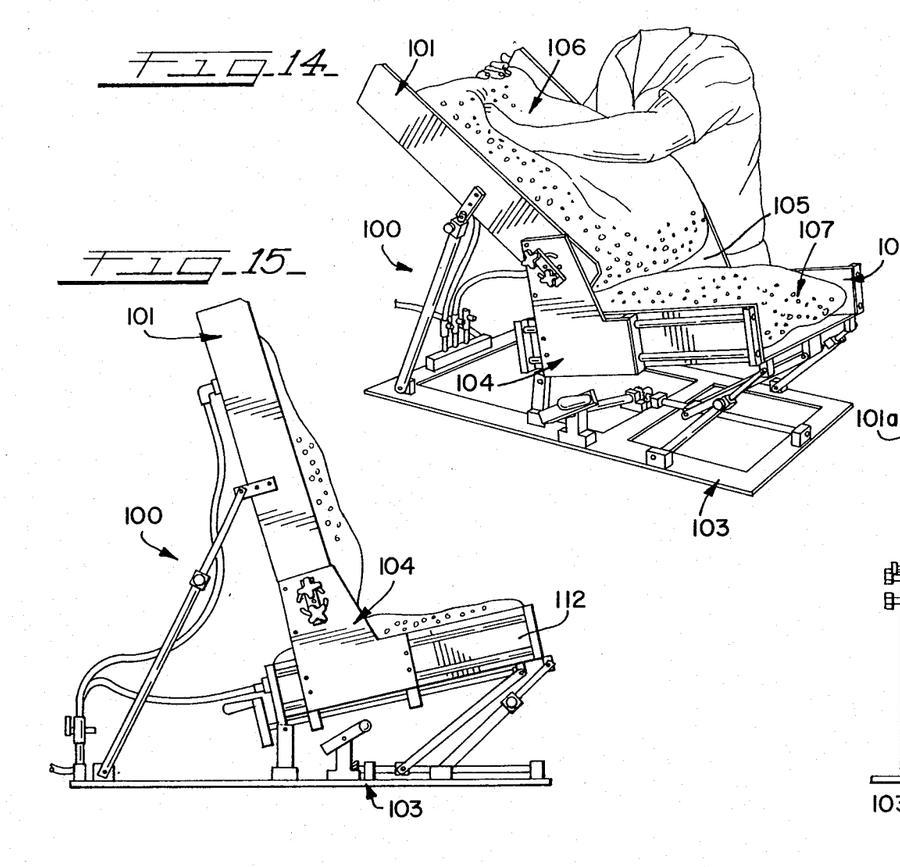
FIG. 14 is a perspective view of the seat-molding frame and beanbag cushions positioned therein being preformed to accept the seating of an individual therein.
FIG. 15 is a side-elevational view of the seat-molding frame shown in FIG. 14.

When custom moulding the seat cushions 60–61, a bean-bag type moulding apparatus, generally indicated at 100, is used. It includes a back-support moulding frame 101, a buttocks-support moulding frame 102 positioned in slidable and angularly adjustable spatial relation thereto, with both being adjustably mounted on a linkage controlled mounting platform 103.

In a manner functionally similar to the living hinges 35, 36 discussed previously, hinge mechanisms 104, 105 (only one shown), provides adjustable angular and lateral positioning of the back-support moulding frame 101 and the buttocks-support moulding frame 102. The back-support moulding frame 101 and buttocks-support moulding frame member 102 are slightly larger than the largest of the stock size cushions made in accordance with the present invention which will fit in commercial wheelchairs. Cushions may be made smaller than the framework of the present invention by cutting the size of the mould made in the frame, as will be described in more detail below. A first bean-bag 106, in this embodiment preferably formed of latex with polyethylene beads (not shown) therein, is mounted on the back-support moulding frame 101, and likewise, a second bean-bag 107, made of identical materials, is mounted horizontally in the buttocks-support moulding frame 102.

A vacuum system includes a manifold 108 mounted on frame platform 103 and having a first vacuum line 110 in fluid communication with the interior of first bean-bag 106. The pressure inside first bean-bag 106 is controlled by a vacuum generator (not shown) which is attached through air line 111 to manifold 108, and a first control valve 112 in line 90. Likewise, a second vacuum line 113 is connected between manifold 108 and second bean-bag 107 and includes a second control valve 114 therein.

Figure 16:
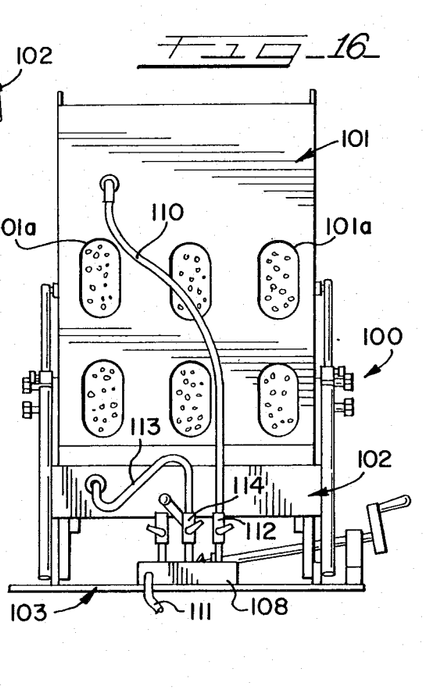
FIG. 16 is a rear-elevational view of the seat-molding frame shown in FIG. 14.

With both moulding frames positioned nearly horizontal, a partial vacuum is drawn through manifold 108 and line 90 into the back-support bean-bag 106. As shown in FIG. 14, once a partial vacuum is achieved, the polyethylene beads in the bag are moved or maneuvered by hand to a position of rough approximation of the cavity desired for the seat user. The amount of vacuum in the bag 106 may be controlled by valve 112 (at about one-half inch Hg) to make the polyethylene beads in the bag 106 highly moveable when the preforming operation begins, and with a vacuum of about 3 inches Hg, the bean bag becomes hard and immobile. Likewise, valve 114 is utilized to control a partial vacuum in bean-bag 107 to rough form the bag to the approximate shape of the user, as shown in FIG. 16, cutouts 101a—101a in the web of back-support moulding frame 81 allow adjacent portions of the bean-bag to be pushed outwardly to aid in properly fitting the bag to the trunk area of the user.

Figure 17:
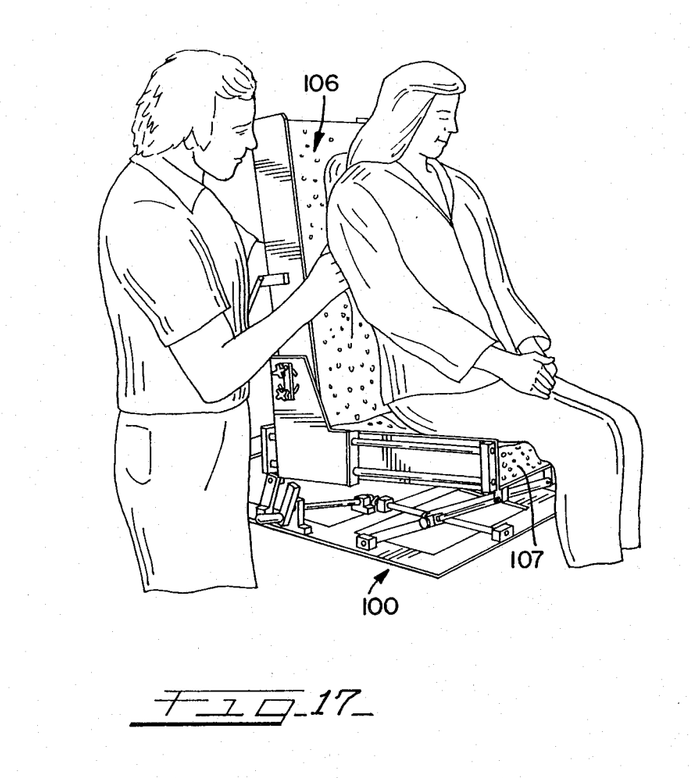
FIG. 17 is a perspective view of the seat-molding frame of the invention having an individual positioned thereon with the beanbag being shaped to the contour of that individual.

As shown in FIG. 17, after the preforming has been completed, the frame 101 is positioned vertically as desired, and an individual for whom custom-molded seat cushions are to be made, is seated on the bean-bags 106, 107. The hands of the moulder, the weight of the proposed cushion user, and control valves 112–114 are all utilized to move the polyethylene beads in the latex bean-bags 86, 87, to ideally fit the shape of the user. After proper fit has been obtained, any desirable corrective shaping of the cushions is made by the moulder and the corrective shaping may be tested on the proposed user, as desired. Once a proper shape for the proposed cushions has been obtained, the control valves 112–114 are adjusted to a vacuum approximating 3 inches Hg, which hardens the bean-bags 106–107 to prevent additional shape change. Thereafter, the individual for whom the cushions are to be made is lifted off of moulding frame 100 and bean-bags 106 and 107.

Figure 18:
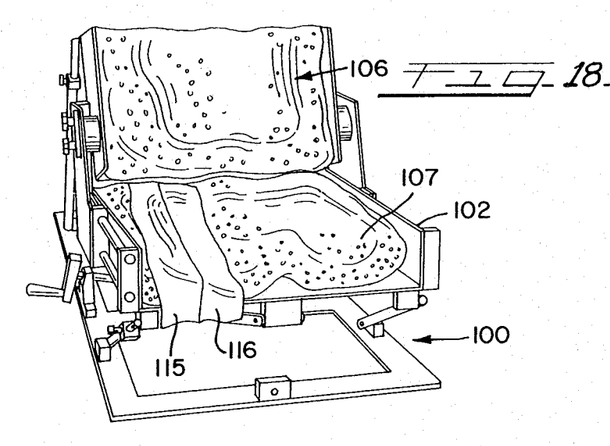
FIG. 18 is a fragmentary-perspective view of the seat shown in FIG. 17 with seat-contour fixed and plaster-mold strips positioned thereover.
Figure 19:
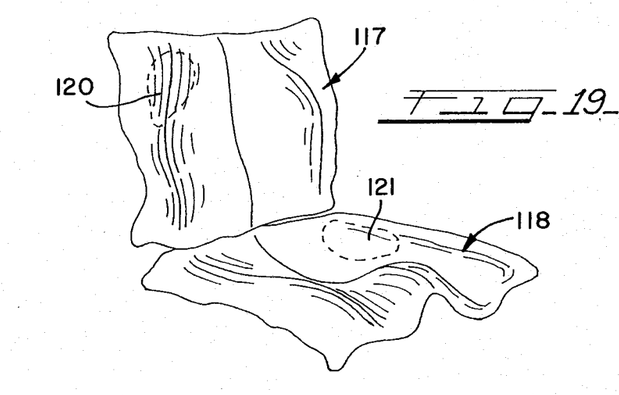
FIG. 19 is a perspective view of the positive-mold impression formed by the plaster gauze strips.

As shown in FIG. 18, plaster impregnated gauze strips 115, 116, are wetted and laid on the bean-bags to make a positive mould of the desired shape of the proposed seat cushion. After the gauze strips 115, 116, are allowed to harden, a positive mould such as that shown at 117, 118, in FIG. 19, is lifted off of the bean-bags. If additional corrective changes need be made to positive moulds 117, 118, or if it appears their shape should be changed for any reason, plaster material may be added to or substracted from the positive moulds as desired, such as, by removal of or addition of materials to areas denoted in circular outline at 120 and 121 on positive moulds 117, 118. It should be noted that it is the back sides (not shown) of mould positive 117 and mould positive 118, which are utilized as the surfaces which the contour of the custom-made cushions will follow. It should be noted that as shown most clearly in FIGS. 14–18, the latex surface of bean-bags 106–107, together with the polyethylene beads thereunder, may, when the bags are drawn to a high vacuum, have a bead-textured surface. This textured surface will translate directly to the positive moulds 117, 118. As the positive mould shells 117, 118, are made of plaster held together by gauze, the back-side surface may be sanded or otherwise worked to provide a smooth surface for the cushions to be made on.

Figures 20, 21, 22:
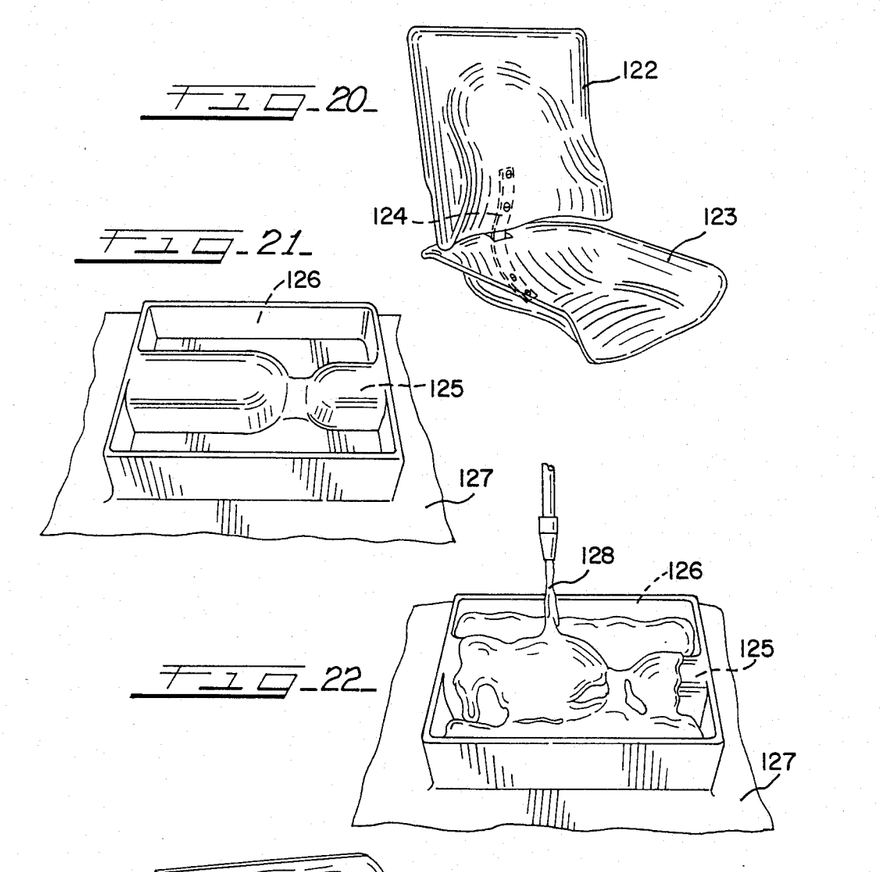
FIG. 20 is a perspective view of a trial-molded seat-shape formed of thermosetting plastic.
FIG. 21 is a perspective view of one of the positive molds shown in FIG. 19 with a mold-frame surrounding same.
FIG. 22 is a perspective view of the mold-frame shown in FIG. 21 with a vinal covering positioned over the mold-frame and having foam material being poured therein.

Referring to FIG. 20, a trial surface for the proposed custom-fitted cushions may be made by laying a heated sheet of thermoplastic material over the back side of mould positives 117, 118 and allowing same to cool. Thus, trial shape back-support member 122 and buttocks-support member 123 may be formed and held together by mounting 124. If the intended user of the cushions is not located in the immediate geographic area where the cushion-making process is taking place, the trial shels 122, 123 may be shipped inexpensively to any location to determine if the proposed seat shape is proper. As the individual is seated in the trial-shape seat 122, 123, any necessary changes may be noted and corrections thereafter made on the mould positives 117, 118, as necessary The trial seat also has another use, as mounting cups (not shown) or other base materials may be affixed to the shell bottom and the seat may be utilized as a bathing seat for the user of the cushions.

As shown in FIGS. 21 and 22, the back-side of a mould positive 125, which is similar to the mould positive 117, 118, disclosed previously, has been cut to a desired rectangular size and thereafter encircled or placed into a frame 126 having depth which is at least the desired depth of the cushion to be made. A sheet of vinyl material 127 is heated and vacuformed inside-out over the back side of the plaster positive 125 and framing material 125 until it conforms to the desired cushion shape and outline. The material extending over the frame may be utilized to protect the frame from any spills or mess-making procedures. As shown in FIG. 22, polyurethane foam 138 is then poured into the frame 126 to a desired depth. It should be noted that the foam expands as it sets and will rise a certain extent. The poured fluid seeks all of the corners and cavities of the mould during the filling process. When the polyurethane foam completely sets, the excess vinyl sheet material 107 is trimmed and one of the custom-formed, seat cushions is completed and appears as shown at 60 and 61 in FIG. 23, the cushions may be press fit into the respective back-supporting frame 33 and/or buttocks-supporting frame 34 of the custom-formed seat 30 of the present invention.

One of the advantages of the seat of the present invention is the expansibility of the seat lengthwise to accommodate growth of the individual for whom the seat is designed, and the expansibility of the seat both lengthwise and widthwise by the relatively inexpensive replacement of one or both custom-formed cushions 60–61, and one or both seat frames if necessary, in the event the individual outgrows the first formed cushions. The custom moulding of second or additional cushions is considerably less expensive than the procurement of a complete new seat should the individual outgrow the seat as originally moulded. Additionally, the custom moulding of seat-back support and buttocks-support cushions provides for substantial surface contact between the individual and the seat, thus minimizing pressure sores, which have heretofore been pronounced where point or small area contact between the user and the seat has been found. Also in one of the most important features of the present invention, the adjustability and custom forming of the seat assembly places the users in a functional position, which is extremely important in cases of severe deformity. The custom-formed seat of the present invention is affixable to various commercial wheelchairs, such as, those sold under the trade marks Everest and Jennings, and Invacare and Stainless Wheelchairs, as well as McLaren and Pogon Strollers.

While one embodiment of the present invention has been shown and described, it will be obvious to those skilled in the art, that changes and modifications may be made within the scope of the present invention. Therefore, it is the aim in the appended claims to cover all such changes and modifications as fall within the true spirit and scope of the invention.

The invention is claimed as follows:

1. A method for forming an individually contoured corrective seat for intended use by a disabled person, said seat being of the type having a frame including a substantially vertical back supporting portion and a substantially horizontal buttocks supporting portion adjustably connected thereto, with each portion adapted to retain at least one resilient cushionlike member thereon, said method comprising the steps of:

positioning a human being on an impression forming structure having back and bottom deformable bags positioned thereon with each bag including a mass of bead-like material therein in order to form impressions on said bags of the back and buttocks respectively of said human being;

evacuating air from said back and bottom bags, respectively, to interlock said bead-like material into a form retaining condition;

forming a positive mold surface of said back and buttocks impressions by applying a setable mastic material to said impressions on said bags, and allowing same to set;

making corrective changes to the shape of said impressions by at least one of manipulating said bead-like material in said bags and repositioning mastic material from at least a portion of said positive mold surface;

forming a mold cavity by providing a boundary wall around the portion of said positive mold surface to be utilized in making a seat cushion; and filling said cavity with a setable fluid material and allowing same to cure into a correctively contoured back and buttocks seat cushions.

2. The method as defined in claim 1 further including the step of:

forming a trial cushion impression by heating a sheet of thermoplastic material and positioning same on said positive mold surface with said sheet conforming to the curvatures of said surface, and allowing said sheet to cool and set; and positioning said human being in said plastic trial impression to ascertain if the proper corrective changes have been made to the positive mold.

3. The method as defined in claim 1 wherein said step of filling said mold cavity includes the step of deforming a sheet of upholstery covering material over said positive mould cavity prior to filling said cavity with setable fluid material.

* * * * *

UNITED STATES PATENT AND TRADEMARK OFFICE
CERTIFICATE OF CORRECTION

PATENT NO. : 4,615,856

DATED : October 7, 1986

INVENTOR(S) : Michael W. Silverman

It is certified that error appears in the above—identified patent and that said Letters Patent is hereby corrected as shown below:

In the Abstract, line 2, "trail" should be -- trial --.

Column 8, line 61, "138" should be -- 128 --.

Signed and Sealed this

Twenty-seventh Day of January, 1987

*Attest:*

DONALD J. QUIGG

*Attesting Officer*     *Commissioner of Patents and Trademarks*

REEXAMINATION CERTIFICATE (2166th)
United States Patent [19]
Silverman

[11] B1 4,615,856

[45] Certificate Issued Dec. 28, 1993

[54] METHOD FOR FORMING AN INDIVIDUALLY CONTOURED CORRECTIVE SEAT FOR A WHEELCHAIR

[75] Inventor: Michael W. Silverman, Chicago, Ill.

[73] Assignee: Pin Dot Products, Niles, Ill.

Reexamination Request:
No. 90/002,844, Sep. 28, 1992

Reexamination Certificate for:
Patent No.: 4,615,856
Issued: Oct. 7, 1986
Appl. No.: 760,245
Filed: Jul. 29, 1985

Certificate of Correction issued Jan. 27, 1987.

[51] Int. Cl.⁵ .................. B29C 33/40; B29C 39/10; B29C 67/22
[52] U.S. Cl. .................. 264/222; 5/653; 5/911; 264/46.8; 264/102; 264/267; 264/322; 264/511; 297/452.28; 297/DIG. 4
[58] Field of Search .................. 264/321, 222, 46.8, 264/511, 102, 267, 322

[56] References Cited

PUBLICATIONS

*Vacuum Dilatancy Casting for the Construction of Individually Molded Seats*, F. H. Germans, M. W. Koster, H. H. Kwee, N. v.d. Mey, R. Soerjanto and D. W. Wijkmans, pp. 1–9, Inter-Clinic Information Bulletin, vol. XIV, No. 5, May 1975.

*A method for Custom Seating of the Severely Disabled*, Charles H. Pritham and Carol I. Leiper, pp. 19–26, Orthotics and Prosthetics, vol. 35, No. 4 Dec. 1981.

*CONTOUR-U, A Custom Total Seating System*, M. W. Silverman, O. Silverman and J. Torossy, p. 91, 5th Annual Conference on Rehabilitation Engineering, Houston, Tex. 1982.

*Individually Customized Postural Support System*, Douglas May, Randall Fincke, Leonard Cancelliere, Jonathan C. Bretz and Steven Gallo, pp. 144–146, Proceedings of International Conference on Rehabilitation Engineering-Toronto, 1980.

*Individually Contoured Seating for the Disabled*, T. V. Strange, J. D. Harris and P. J. R. Nichols, pp. 86–88, Rheumatology and Rehabilitation, 1978.

*Reusable Casting Technique for Customized Total Contact Seating*, James R. O'Reagan and David F. Law, pp. 153–155, Proceedings of International Conference on Rehabilitation Engineering-Toronto, 1980.

*Modern Orthotics for Spinal Deformities*, Robert B. Winter and J. Martin Carlson, pp. 74–86, Clinical Orthopedics and Related Research, No. 126, Jul./Aug. 1977.

*Supportive Seating for the Handicapped*, R. L. Nelham pp. 379–381 Biomedical Engineering, vol. 10, No. 10 Oct. 1975.

*Vacuum-formed Orthoses for Fracture of the Tibia*, Melvin Stills pp. 43–55 Orthotics and Prosthetics, vol. 30, No. 2 Jun. 1976.

*Primary Examiner*—Richard L. Chiesa

[57] ABSTRACT

An improved method for making custom molded seat cushions wherein a bead-filled latex bag is used as a trial buttocks supporting cushion and likewise another bead-filled latex bag is used as back-supporting cushion in a frame which is similar in function to the seat frame of the chair. An impression of a desired portion of a user's body is formed on each of the bags and air is removed from the bags thereafter to fix the impression. A positive mold of the individual's respective backside and buttocks impression are made. Corrective changes may be made either to the latex bag impression as it is being formed or the positive mold impression. The positive mold impression is then utilized along with a mold frame to mold a custom fitted seat cushion for the individual who will utilize the wheelchair. The cushions are then press fit into their respective seat frames and an individualized custom molded wheelchair seat is formed which provides for correctively positioning the individual in full surface contact between the body and seat to minimize or rid the possibility of bed sores, and to place the client in a functional position.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 28-38:

As shown most clearly in FIGS. 1-4, each L-shaped hinge 35, 36 (with hinge 35 shown for explanation) includes a horizontally-extending base [61] *65* and a vertically-extending arm portion [62] *66*. Adjacent the distal end of the base 65 are a pair of arcuate slots 67a-67b, adjustably retained by threaded fasteners 67—67. Adjacent the distal end of the upwardly-extending arm member 66 are a second pair of arcuate slots 68a-68b, adjustably retained by threaded fasteners 68—68. An aperture 69 on L-shape hinge 35 may be used as [s] *a* seat belt mounting, as shown in FIG. 3.

AS A RESULT OF REEXAMINATION, IT HAS BEEN DETERMINED THAT:

Claim 3 is cancelled.

Claims 1 and 2 are determined to be patentable as amended.

1. A method for forming an individually contoured corrective seat for intended use by a disabled person, said seat [being of the type] having a frame including a substantially vertical back supporting portion and a substantially horizontal buttocks supporting portion adjustably connected thereto, with each portion [adapted to retain] *having means for retaining* at least one resilient [cushionlike] *cushion* member thereon, said method comprising the steps of:

positioning a human being on an impression forming structure having back and bottom deformable bags positioned thereon with each bag including a mass of [bead-like] *bead* material therein in order to form impressions on said bags of the back and buttocks respectively of said human being;

evacuating air from said back and bottom bags, respectively, to interlock said [bead-like] *bead* material into a form retaining condition;

*lifting off said human being from said impression forming structure;* forming a positive mold surface of said back and buttocks impressions by applying a setable mastic material to said impressions on said bags, and allowing same to set;

making corrective changes to the shape of said impressions by at least one of manipulating said [bead-like] *bead* material in said bags and repositioning mastic material from at least a portion of said positive mold surface;

forming a mold cavity by providing a boundary wall around the portion of said positive mold surface to be utilized in making a seat cushion; and filling said cavity with a setable fluid material and allowing same to cure into [a] correctively contoured back and buttocks seat cushions *including the step of deforming a sheet of upholstery covering material over said positive mold cavity prior to filling said cavity with said setable fluid material such that said upholstery covering material is deformed so as to conform with a desired cushion shape.*

2. The method as defined in claim 1 further including the step of:

forming a trial cushion impression by heating a sheet of thermoplastic material and positioning same on said positive mold surface with said sheet conforming to the curvatures of said surface, and allowing said sheet to cool and set; and

[positioning] *repositioning* said human being in said plastic trial impression to ascertain if the proper corrective changes have been made to the positive mold.

* * * * *